United States Patent
Eisner

(10) Patent No.: US 10,391,209 B2
(45) Date of Patent: Aug. 27, 2019

(54) SYSTEM AND METHOD FOR GUIDED REMOVAL FROM AN IN VIVO SUBJECT

(71) Applicant: THE GENERAL HOSPITAL CORPORATION, Boston, MA (US)

(72) Inventor: Brian Howard Eisner, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/354,457

(22) Filed: Nov. 17, 2016

(65) Prior Publication Data

US 2017/0065752 A1 Mar. 9, 2017

Related U.S. Application Data

(63) Continuation of application No. 14/774,418, filed as application No. PCT/US2014/026037 on Mar. 13, 2014, now abandoned.
(Continued)

(51) Int. Cl.
*A61B 17/22* (2006.01)
*A61M 1/00* (2006.01)
*A61B 18/00* (2006.01)

(52) U.S. Cl.
CPC ........... *A61M 1/0058* (2013.01); *A61B 17/22* (2013.01); *A61B 17/22031* (2013.01);
(Continued)

(58) Field of Classification Search
CPC ............. A61B 17/22; A61B 17/22031; A61B 2017/22038; A61B 2017/22079; A61B 2018/00505; A61B 2018/00511; A61B 2018/00517; A61B 17/221; A61B 2217/005; A61M 1/0058; A61M 1/0033;
(Continued)

(56) References Cited

U.S. PATENT DOCUMENTS 3,830,240 A * 8/1974 Antonevich ..... A61B 17/22012
601/4
4,601,713 A * 7/1986 Fuqua ............... A61M 25/0023
604/103.14
(Continued)

FOREIGN PATENT DOCUMENTS

CN 203988361 U 12/2014
WO 2010068467 A1 6/2010

OTHER PUBLICATIONS

Villanueva, et al., Silicone Catheters May Be Superior to Latex Catheters in Difficult Urethral Catherization After Urethral Dilation, Journal of Endourology, 2011, 25(5):841-844.
(Continued)

*Primary Examiner* — Ryan J. Severson
*Assistant Examiner* — Christian D Knauss
(74) *Attorney, Agent, or Firm* — Quarles & Brady LLP

(57) ABSTRACT

A device for removing objects from an in vivo subject includes vacuum tube adapted to be associated with a sheath sized to be inserted into a passageway of the subject. The vacuum tube provides a suction channel extending therethrough. A navigation mechanism is designed to guide the vacuum tube through the passageway. The removal device is designed to remove debris having an approximate diameter of between about 0.0001 mm to about 8 mm.

17 Claims, 5 Drawing Sheets

Related U.S. Application Data

(60) Provisional application No. 61/783,239, filed on Mar. 14, 2013.

(52) U.S. Cl.
CPC ........... *A61B 2017/22038* (2013.01); *A61B 2017/22039* (2013.01); *A61B 2017/22079* (2013.01); *A61B 2018/00511* (2013.01)

(58) Field of Classification Search
CPC ............ A61M 1/0035; A61M 1/0037; A61M 1/0039; A61M 1/0041; A61M 1/0047
See application file for complete search history.

(56) References Cited

U.S. PATENT DOCUMENTS

| | | | |
|---|---|---|---|
| 4,802,461 A | 2/1989 | Cho | |
| 4,874,360 A | 10/1989 | Goldberg et al. | |
| 5,476,450 A * | 12/1995 | Ruggio | A61B 17/22 604/104 |
| 5,827,229 A | 10/1998 | Auth et al. | |
| 6,395,021 B1 | 5/2002 | Hart et al. | |
| 7,540,868 B2 | 6/2009 | Elliott et al. | |
| 7,654,989 B2 | 2/2010 | Knapp | |
| 7,883,515 B2 | 2/2011 | Kear | |
| 8,192,500 B2 | 6/2012 | Chung | |
| 8,597,261 B2 | 12/2013 | Knapp | |
| 8,672,928 B2 | 3/2014 | Liu et al. | |
| D715,921 S | 10/2014 | Wan | |
| 8,858,569 B2 | 10/2014 | Wan | |
| 8,911,415 B2 | 12/2014 | Knapp | |
| 9,295,811 B2 | 3/2016 | Knapp | |
| 2003/0199986 A1 | 10/2003 | McWeeney et al. | |
| 2003/0216760 A1 * | 11/2003 | Welch | A61B 17/22 606/159 |
| 2004/0019358 A1 | 1/2004 | Kear | |
| 2004/0153095 A1 | 8/2004 | Seddon | |
| 2004/0267213 A1 * | 12/2004 | Knapp | A61B 1/307 604/284 |
| 2005/0143678 A1 | 6/2005 | Schwarz et al. | |
| 2005/0149201 A1 | 7/2005 | McWeeney et al. | |
| 2007/0298069 A1 | 12/2007 | Bucay-Couto et al. | |
| 2008/0004578 A1 | 1/2008 | Hixon et al. | |
| 2009/0163846 A1 * | 6/2009 | Aklog | A61B 17/22 604/5.02 |
| 2010/0137846 A1 | 6/2010 | Desai et al. | |
| 2010/0305475 A1 | 12/2010 | Hinchliffe et al. | |
| 2011/0060315 A1 | 3/2011 | Windheuser et al. | |
| 2011/0224489 A1 | 9/2011 | Deal | |
| 2011/0245841 A1 | 10/2011 | Shohat et al. | |
| 2013/0024003 A1 | 1/2013 | McWeeney et al. | |
| 2013/0165944 A1 | 6/2013 | Gal et al. | |
| 2016/0001050 A1 | 1/2016 | Yee et al. | |
| 2016/0120557 A1 | 5/2016 | Goddard et al. | |
| 2017/0215899 A1 | 8/2017 | Harrah et al. | |
| 2017/0215964 A1 | 8/2017 | Harrah et al. | |
| 2017/0215965 A1 | 8/2017 | Harrah et al. | |

OTHER PUBLICATIONS

International Search Report and Written Opinion dated Sep. 16, 2014 in connection with PCT/US2014/026037.
European Patent Office, Extended European Search Report, Application No. 14775184.6, dated Nov. 17, 2016.
PCT International Search Report and Written Opinion, PCT/US2014/025321, dated Jul. 18, 2014.
European Patent Office, Extended European Search Report, Application No. 18205890.9, dated Jan. 29, 2019, 5 pages.

* cited by examiner

SYSTEM AND METHOD FOR GUIDED REMOVAL FROM AN IN VIVO SUBJECT

CROSS-REFERENCE TO RELATED APPLICATIONS

The present application is a continuation of U.S. Application Ser. No. 14/774,418 filed Sep. 10, 2015 which represents the national stage entry of PCT International Application No. PCT/US2014/026037 filed Mar. 13, 2014, which is based on, and claims priority to, U.S. Provisional Application Ser. No. 61/783,239, filed Mar. 14, 2013, all of which are incorporated herein by reference in their entirety for all purposes.

STATEMENT REGARDING FEDERALLY SPONSORED RESEARCH

N/A

BACKGROUND OF THE INVENTION

The present invention relates to systems and methods for the guided removal of objects in vivo. In particular, the invention is directed to a removal device adapted to traverse compact areas utilizing a navigation mechanism, and more specifically, to capture and/or remove debris through a vacuum tube that is in communication with a suction source.

Kidney stones are a common medical problem that negatively impact millions of individuals worldwide. Kidney stones include one or more solid masses of material that are usually made of crystals and form in parts of the urinary tract including in the ureter, the kidney, and/or the bladder of the individual. Kidney stones range in size from smaller (less than about 1 cm) to very large (more than 4 cm) and may cause significant pain to the individual and damage to the kidney. The overwhelming majority of stones that are treated by surgeons are less than 1 cm.

The recommended treatment for removal of the kidney stones varies according to numerous factors including the size of the kidney stones, the number of kidney stones, and the location of the kidney stones. The most common treatments for kidney stones are shock wave lithotripsy (ultrasound waves used to fracture the stones), ureteroscopy (fracture and removal of the stones using an endoscope that is introduced through the bladder), and percutaneous nephrolithotomy (fracture and removal of the stones using an endoscope that is introduced through a sheath placed through the patient's back into the kidney).

The largest kidney stones are usually removed through percutaneous nephrolithotomy or nephrolithotripsy, or through other similar procedures. In these procedures, a small incision is made through the patient's back adjacent the kidney and a sheath is passed into the kidney to accommodate a larger endoscope used to fracture and remove stones. The stone may be removed directly through the tube or may be broken up into small fragments while still in the patient's body and then removed via a vacuum or other known methods (nephrolithotripsy).

There are numerous drawbacks associated with nephrolithotomy, nephrolithotripsy, and other invasive surgeries requiring an incision in the skin. Namely, such surgical techniques may require significantly more anesthesia administered to the patient, the surgeries are more complicated and pose a higher risk of infection and complications for the patient, and the surgeries require a substantial incision in the patient, which may leave a scar. Additionally, given the invasiveness of the procedure, percutaneous procedures are usually not preferred for smaller kidney stones (e.g., less than 1 cm) depending on the size and location of the stones.

In contrast, traditionally, smaller kidney stones have been treated using other, less invasive techniques including through ureteroscopy. In ureteroscopy, the surgeon typically inserts a ureteroscope into the urethra through the bladder and the ureter to provide the surgeon with a direct visualization of the kidney stone(s) which may reside in the ureter or kidney. The surgeon then removes the kidney stone directly using a basketing device if the kidney stone is small enough to pass through the urinary tract without difficulty, or the surgeon fractures the kidney stone into smaller pieces using a laser or other breaking device. After breaking the kidney stone into smaller pieces, the surgeon removes the laser or breaking device and inserts a basket or other object to capture the kidney stone fragments. Upon retrieving some of the kidney stone fragments, the surgeon removes the basket from the patient and empties the kidney stone fragments therefrom. This process is repeated until all kidney stones and kidney stone fragments are broken up and removed from the body.

It should be apparent that this process is extremely time consuming, costly, and inefficient because the surgeon is required to insert and remove the scope and basket into and out of the patient many times to completely remove the kidney stones and kidney stone fragments therefrom. Using a basket removal device to capture kidney stones or kidney stone fragments suffers from other drawbacks in that the basket is difficult to position adjacent the kidney stone fragments and maneuver in a manner that effectively retrieves the fragments. The training required for such a procedure is not insignificant and the aforementioned basket removal technique is difficult for even the most skilled surgeons. Additionally, the surgeon is susceptible to hand fatigue due to the extended amount of time required to operate the kidney stone retrieval baskets. Further, the patient is required to be under local anesthesia and/or remain immobile over an extended amount of time. Still further, the basket retrieval devices cause irritation to the urinary tract due to the repeated insertion and removal therefrom.

Other kidney stone removal techniques may utilize suction devices to remove kidney stones and kidney stone fragments from the patient. Such techniques use a flexible tube designed to be disposed within a working channel of a ureteroscope. The flexible tube is designed to have a diameter of between 2 french and 3 french and includes a suction source therethrough. Utilization of this type of device necessarily restricts the size of the passageway available to remove kidney stones and portions thereof from the patient. Indeed, the diameter of the ureteroscope occupies a significant portion of the limited passageway into the patient. Therefore, the size of the flexible tube is bounded by the size of the working channel of the ureteroscope and is defined by a diameter of under about 3 french. The utilization of the working channel of a ureteroscope or other viewing instrument has heretofor been utilized to assist the surgeon in locating the matter to be removed from the patient and to assist in guiding the removal instruments to an appropriate location. The use of these devices is necessarily restricted to removal of debris that is smaller than the size of the tube disposed in the working channel (i.e., under about 3 french). Accordingly, the prior art devices of this type are unable to remove debris greater than about 2 mm and removal of even smaller stones becomes problematic given the narrow lumen size in the prior art devices and their resulting propensity to clog, even with stones of 1 mm or less.

SUMMARY OF THE INVENTION

The present invention overcomes the aforementioned drawbacks by providing a way to guide a removal device into position inside of a patient in a manner that does not necessarily require a viewing instrument. The elimination of the access approach using the working channel in the viewing device, as currently known in the art, provides numerous advantages over the prior art devices because it allows the removal device to have a larger diameter and is capable of removing kidney stone that are clinically significant (e.g., both small and larger kidney stones) and kidney stone fragments as a result thereof. Further advantages are realized through the use of a navigation mechanism that assists the surgeon in positioning the device without the use of a viewing instrument (although a viewing instrument or other viewing techniques could be used in conjunction with the device, if desired). The diameter parameter of the device is designed to allow removal of debris and kidney stones characterized as dust fragments to greater than about 2.5 mm in diameter.

In one configuration, a removal device includes vacuum tube adapted to be associated with a sheath sized to be inserted into a passageway of the subject. The vacuum tube provides a suction channel extending therethrough. A navigation mechanism is designed to guide the vacuum tube through the passageway. The removal device is designed to remove debris having an approximate diameter of between about 0.0001 mm to about 8 mm.

In a different configuration, a removal device for use in a human urinary tract includes a sheath designed to be positioned in the urinary tract. A vacuum tube is disposed at least partially within the sheath, wherein the vacuum tube is characterized by a diameter of about 10 Fr. to about 18 Fr. A valve is in communication with a suction source, wherein the valve is adapted to regulate suction supplied to the vacuum tube.

In another configuration, a method of removing an object includes the steps of positioning a sheath in a passageway and inserting a device into the passageway adjacent the object to break the object into fragments. The method further includes the steps of removing the device from the passageway, guiding a vacuum tube through the sheath adjacent the fragments of the object, and applying a suction to remove the fragments of the object.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
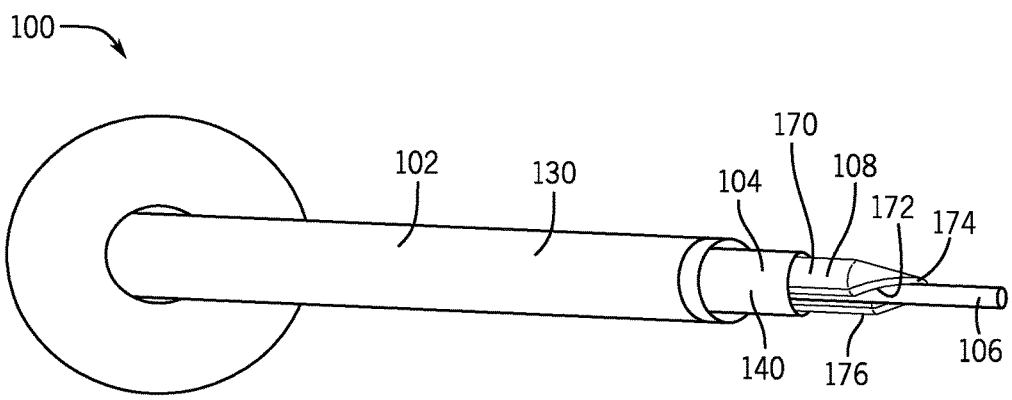
FIG. 1 is an isometric view of a removal device including a sheath, a vacuum tube, an introducer, and a navigation mechanism.

Referring generally to FIGS. 1-8, a removal device 100 includes a sheath 102, a vacuum tube 104, and a navigation mechanism 106. The removal device 100 optionally includes an introducer core 108 adapted to assist in positioning one or more portions of the removal device 100 in a passageway. The removal device 100 further optionally includes a valve 110 that is in communication with, and assists in controlling suction that is supplied to the vacuum tube 104. One or more of the sheath 102, navigation mechanism 106, and/or introducer core 108 may be optional for use with the removal device 100. For example, in one configuration, the sheath 102 is omitted from the removal device 100.

Figure 7:
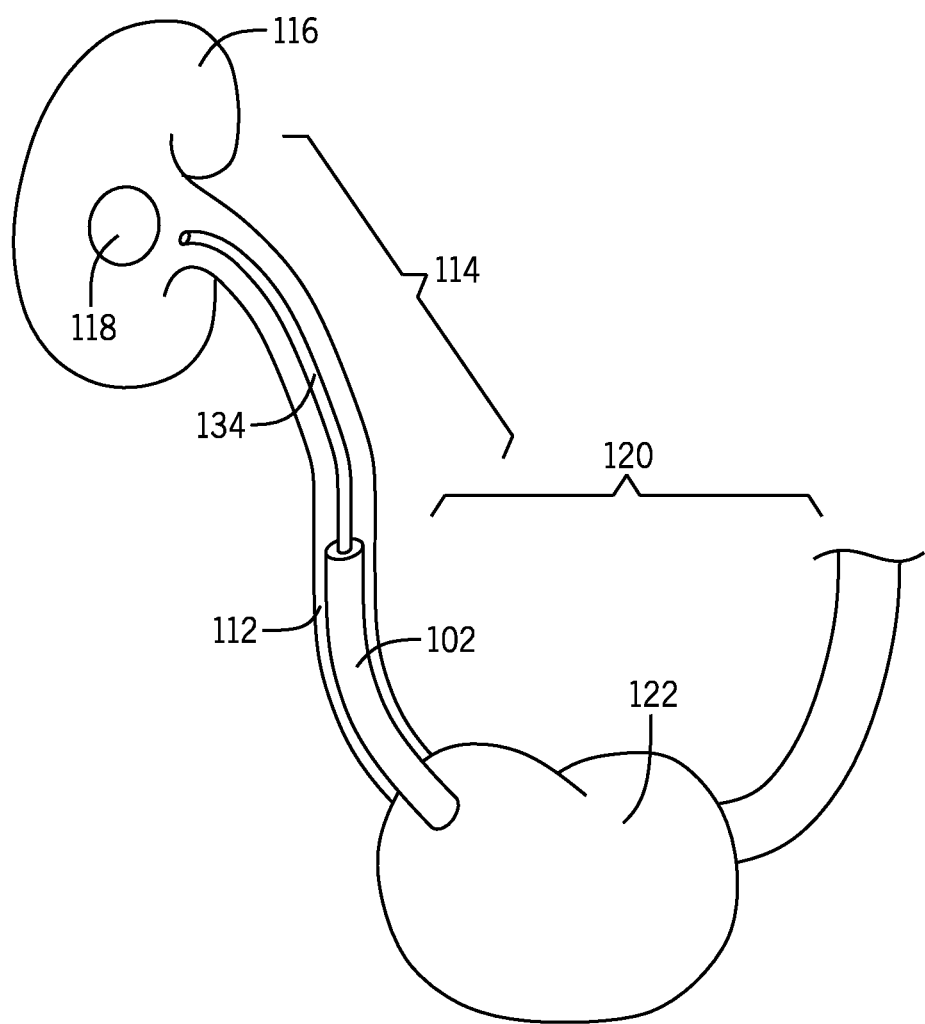
FIG. 7 is a partial schematic view depicting a possible installation of a removal device in a urinary tract of a patient in a first state, wherein a ureteroscope is disposed in the sheath of FIG. 1 adjacent a kidney stone.
Figure 8:
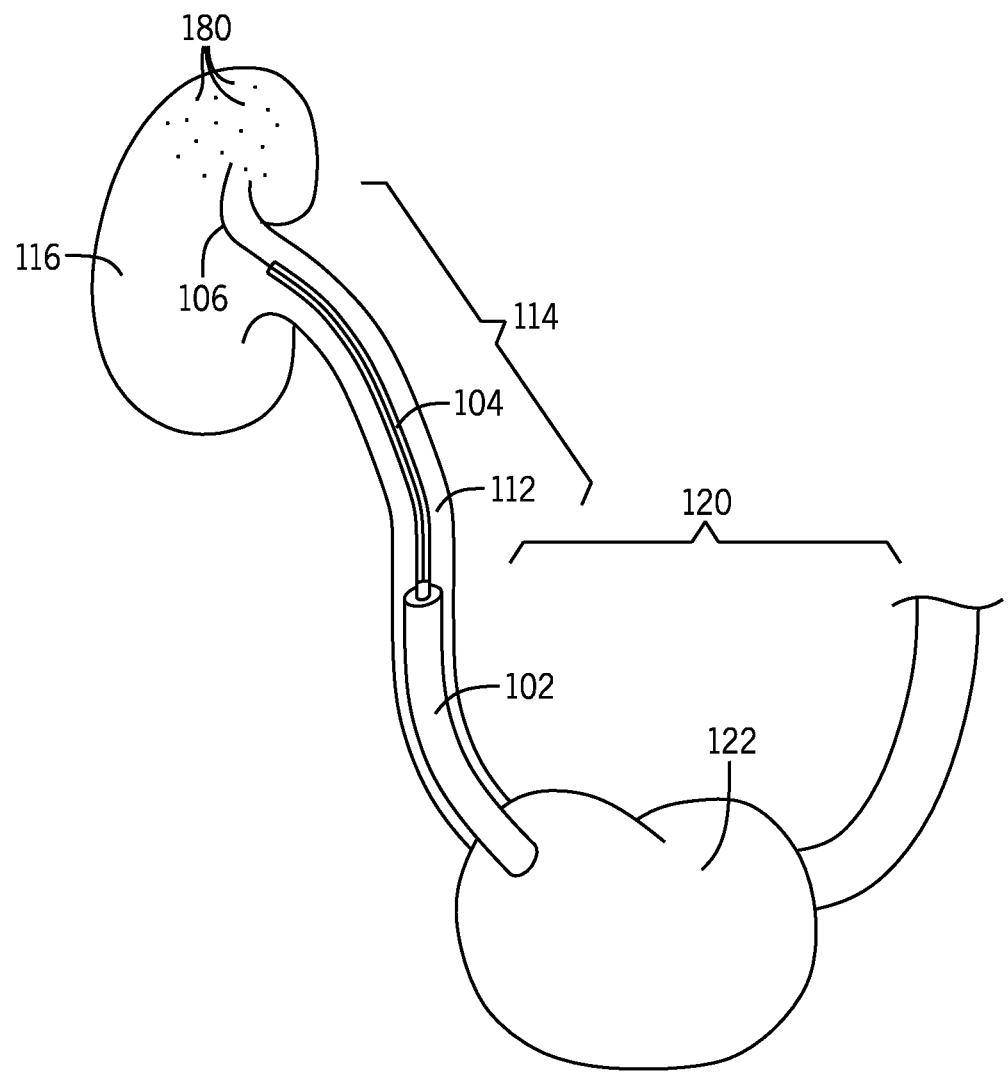
FIG. 8 is a partial schematic view of the removal device of FIG. 7 in a second state, wherein the vacuum tube and navigation mechanism of FIG. 1 is disposed adjacent kidney stone fragments.

As best seen in FIGS. 7 and 8, the removal device 100 is designed to be positioned in a passageway of a patient (e.g., urinary tract), and in particular, into a patient's ureter 112. The removal device 100 includes a renal end 114 designed to be positioned proximate the patient's kidney 116, and more particularly, adjacent to one or more kidney stones 118. The removal device 100 includes a bladder end 120 that is designed to extend through the bladder 122 and out of the patient through the urethra (not shown). The removal device 100 provides an uninterrupted passageway from the kidney stones 118 or kidney stone fragments in the kidney 116, through the ureter 112 and bladder 122, and out of the patient.

Figure 2:
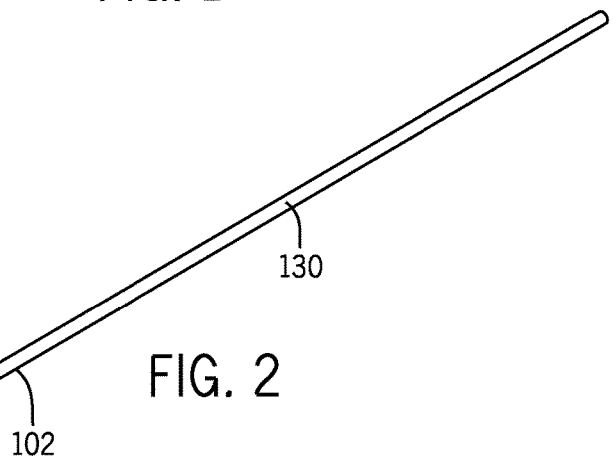
FIG. 2 is an isometric view of a sheath of the removal device of FIG. 1.

Now turning to FIGS. 1 and 2, the sheath 102 is provided as at least one substantially cylindrical tube 130 defining a lumen. The tube 130 includes at least one passageway 132 extending substantially longitudinally therethrough, although additional passageways may be included in the sheath 102 as desired. The passageway 132 extends through the entirety of the sheath 102 and is adapted to receive a ureterscope 134 (see FIG. 7) and/or other viewing instrument. The ureterscope 134 preferably includes a laser (not shown) or other mechanism that fractures the kidney stone 118 into smaller fragments (or dust). The passageway 132 is also designed to accommodate the vacuum tube 104 and/or navigation mechanism 106 therein, as described in more detail hereinbelow. The tube 130 is preferably substantially cylindrical to conform to the orifice and/or passageway of the patient in which the removal device 100 is designed to be utilized. In other configurations, the tube 130 includes other shapes as desired. It should also be noted that the sheath 102 may be omitted from the removal device 100 all together such that the vacuum tube 104 is utilized and serves the function of the sheath 102, which is discussed hereinbelow.

The sheath 102 is preferably made of a biocompatible material that is rigid enough to support the other components of the removal device 100 (e.g., the vacuum tube 104 and navigation mechanism 106), but elastic enough to conform to the contours of the passageway of the patient. For example, suitable materials for use as the sheath 102 include polymers and copolymers such as polyurethane, polyvinyl chloride, polyethylene, polypropylene, and polyamides. Other useful materials include other biocompatible plastics, e.g., polyester, nylon based biocompatible polymers, polytetrafluoroethylene polymers, silicone polymers, and other thermoplastic polymers.

The sheath 102 is preferably defined by a length dimension of about 15 cm to about 45 cm. In a different configuration, the sheath 102 includes a length dimension of about 20 cm to about 35 cm. In a further configuration, the sheath 102 has a length dimension of about 25 cm to about 30 cm. It should be apparent that the length of the sheath 102 may be adjusted in view of numerous factors including, for example, patient size.

The sheath 102 is further defined by an interior diameter dimension of the tube 130. In one configuration, the interior diameter of the tube 130 is between about 2 Fr. to about 30 Fr. In a different configuration, the interior diameter of the tube 130 is between about 10 Fr. to about 16 Fr. In another configuration, the interior diameter is between about 12 Fr. to about 14 Fr.

Figure 3:
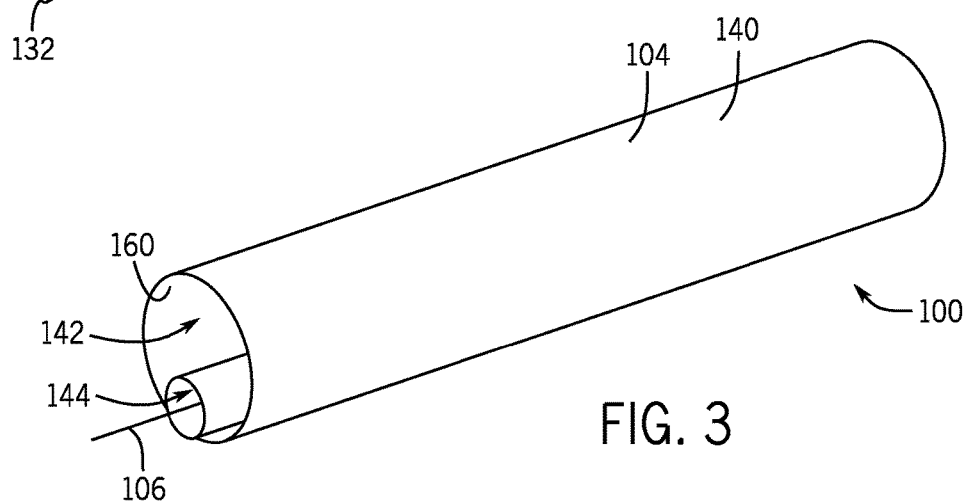
FIG. 3 is an isometric view of the vacuum tube and navigation mechanism of FIG. 1.
Figure 4:
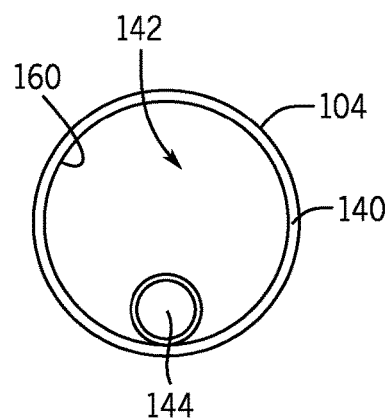
FIG. 4 is a front elevational view of the vacuum tube of FIG. 3, with the navigation mechanism removed therefrom for clarity.

Now turning to FIGS. 3 and 4, the vacuum tube 104 is characterized by an elongate dual lumen 140 defined by a first (larger) passageway 142 and a second (smaller) passageway 144 extending longitudinally therethrough. The vacuum tube 104 may optionally include a specialized tip (not shown) at an end thereof that assists in maintaining the patency of the vacuum tube 104. The tip may also allow the vacuum tube 104 to be positioned in areas that are difficult to access (e.g., the lowest part of the kidney).

The first passageway 142 is designed to accommodate the introducer 108, which is used to assist in positioning one or more portions of the removal device 100 in the patient, as explained in more detail hereinbelow. The first passageway 142 is also designed to accommodate the suction provided from a suction source 148 (see FIG. 6) that is utilized with the removal device 100. The first passageway 142 of the vacuum tube 104 guides the suction to an area adjacent the kidney stones 118 (and/or kidney stone fragments) and facilitates the kidney stones 118 being removed therethrough. The first passageway 142 acts as a primary passageway for removal of the kidney stones 118 (and/or kidney stone fragments).

Still referring to FIGS. 3 and 4, the second passageway 144 of the vacuum tube 104 is disposed adjacent an internal surface 160 of the lumen 140 and is designed to accommodate the navigation mechanism 106 as shown in FIG. 3. In a different configuration, the second passageway 144 may also accommodate a ureterscope or other viewing instrument. In still a further configuration, the second passageway 144 may accommodate other devices that may be utilized in conjunction with the removal device. For example, in one particular configuration, a miniature camera, ureteroscope, or other visualization device may be utilized through either the first or second passageway 142, 144. Although depicted adjacent the internal surface 160, the second passageway 144 may be disposed in any other location within the vacuum tube 104, or may be omitted all together. Further, the size of the first and second passageways 142, 144 may be adjusted as desired.

In a different configuration, the removal device 100 and/or vacuum tube 104 includes additional lumens extending therethrough. For example, in one configuration, the removal device 100 includes a first passageway adapted to receive a suction source, a second passageway adapted to receive a camera or other visual aid, and a third passageway adapted to receive a guidewire.

The vacuum tube 104 is preferably made of a flexible biocompatible material such that the vacuum tube 104 is able to move through the contours of the passageway of the patient. The vacuum tube 104 is preferably made of a material that is not susceptible to kinks and knots during insertion, use, and removal. For example, in some configurations, the vacuum tube 104 is constructed of a thermoplastic elastomer, or a natural or synthetic polymer such as silicone. In other configurations, suitable materials for use include other polymers and copolymers such as polyurethane, polyvinyl chloride, polyethylene, polypropylene, and polyamides. Other useful materials include other biocompatible plastics, e.g., polyester, nylon based biocompatible polymers, polytetrafluoroethylene polymers, silicone polymers, and other thermoplastic polymers.

One or more portions of the vacuum tube 104 may include a coating and/or may comprise a hydrophilic or hydrophobic material. The coating may assist in positioning the vacuum tube 104 within the sheath 102, positioning the navigation mechanism 106 within the vacuum tube 104, and/or assisting in debris removal through the first passageway 142.

The vacuum tube 104 may also include a reinforcement mechanism (not shown) along a portion (or all) thereof that assists in maintaining the patency and the flexibility thereof. In one configuration, the reinforcement mechanism is provided in the form of a spiral or non-spiral wire. In a different configuration, the reinforcement mechanism is provided in other forms as known in the art.

In one configuration, the vacuum tube 104 includes a hydrophilic or hydrophobic coating and the vacuum tube 104 is used without the sheath 102. In a different configuration, the vacuum tube 104 is designed to be disposed at least partially within the sheath 102 during use. Therefore, the circumference of the vacuum tube 104 is smaller than that of the sheath 102. The lumen 140 of the vacuum tube 104 is defined by a diameter of between about 3 Fr. to about 30 Fr., more preferably between about 10 Fr. to about 18 Fr., and most preferably between about 11 Fr. to about 13 Fr. In one configuration, the lumen 140 of the vacuum tube 104 is about 10 Fr. In a different configuration, the lumen 140 of the vacuum tube 104 is about 11 Fr. In still a different configuration, the lumen 140 of the vacuum tube 104 is about 12 Fr.

The diameter of the second passageway 144 of the vacuum tube 104 is smaller than the diameter of the lumen 140 and is characterized by a diameter of between about 0.5 Fr. to about 8 Fr., and more preferably between about 3 Fr. to about 6 Fr. In one configuration, the second passageway 144 of the vacuum tube 104 is about 3 Fr. In a different configuration, the second passageway 144 of the vacuum tube 104 is about 4 Fr. In still a different configuration, the first passageway 144 of the vacuum tube 104 is about 7 Fr.

Still referring to FIG. 3, as discussed previously, the second passageway 144 of the vacuum tube 104 is designed to accommodate the navigation mechanism 106 as shown in FIG. 3. The navigation mechanism 106 is preferably provided in the form of a guidewire. Guidewires suitable for use in the removal device 100 are characterized by a diameter of between about 0.014 in. to about 1 in. In one configuration, the guidewire is characterized by an elongate flexible material having a diameter of about 0.035 in. or about 0.038 in. Guidewires suitable for use with the removal device 100 include, for example, the Sensor' guidewire provided by Boston Scientific (Natick, Mass.), or the Glidewire™ provided by Terumo International Systems (Tokyo, Japan). Additionally, the removal device 100 may be utilized in conjunction with the guidewire described in U.S. patent application Ser. No. 12/660,891, filed on Mar. 5, 2010, and incorporated by reference in its entirety. In other configurations, the navigation mechanism 106 may comprise other devices or mechanisms that assist in positioning portions of the removal device 100.

The vacuum tube 104 and/or other portions of the removal device 100 may be controlled using various control mechanisms. For example, in one configuration, the vacuum tube 104 is controlled using a knob, a lever, a button, a foot pedal, combinations thereof, and the like. Various operational parameters may be controlled with the aforementioned control mechanisms including positioning and/or navigating one or more components of the vacuum tube 104, and/or controlling (e.g., increasing or decreasing) the level of suction.

In one configuration, the guidewire is designed to be inserted into the patient and navigated to the kidney 116. The removal device 100 is passed over the guidewire through one of the passageways described herein (e.g., the second passageway 144). In some instances, the sheath 102 is optionally inserted into the patient first, followed by one or more of the guidewire and/or removal device 100.

In a different configuration, the removal device 100 is designed to interact with and pass over the guidewire. In one configuration, the guidewire is inserted into the sheath 102. In a different configuration, the guidewire is inserted into a portion of the vacuum tube 104 (e.g., through the first or second passageway 142, 144, respectively). The guidewire may be utilized in one or more of the passageways in the removal device 100. In a preferred configuration, the guidewire is initially inserted into the flexible tube 130 of the sheath 102 in conjunction with the ureterscope 134. The guidewire is also preferably utilized in conjunction with the second passageway 144 as a guidance mechanism for the vacuum tube 104 as described in more detail hereinbelow.

Figure 5:
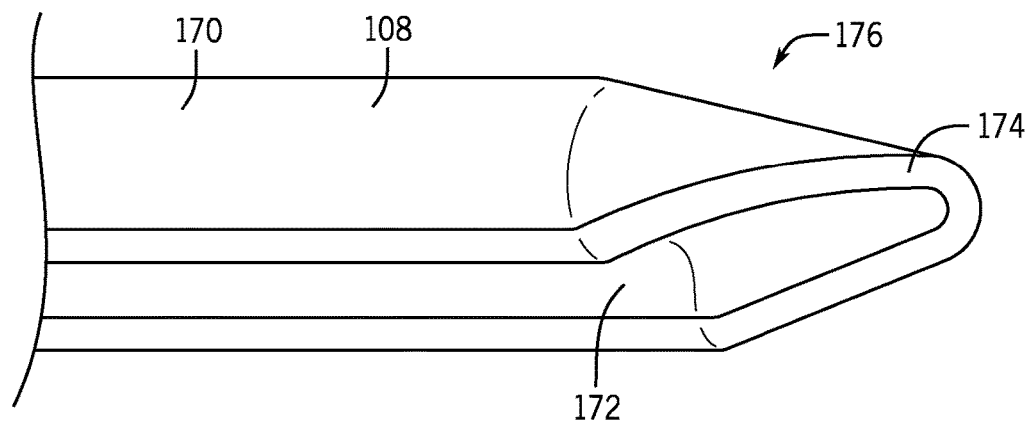
FIG. 5 is a partial isometric view of the introducer of the removal device of FIG. 1 enlarged for magnification purposes.
Figure 6:
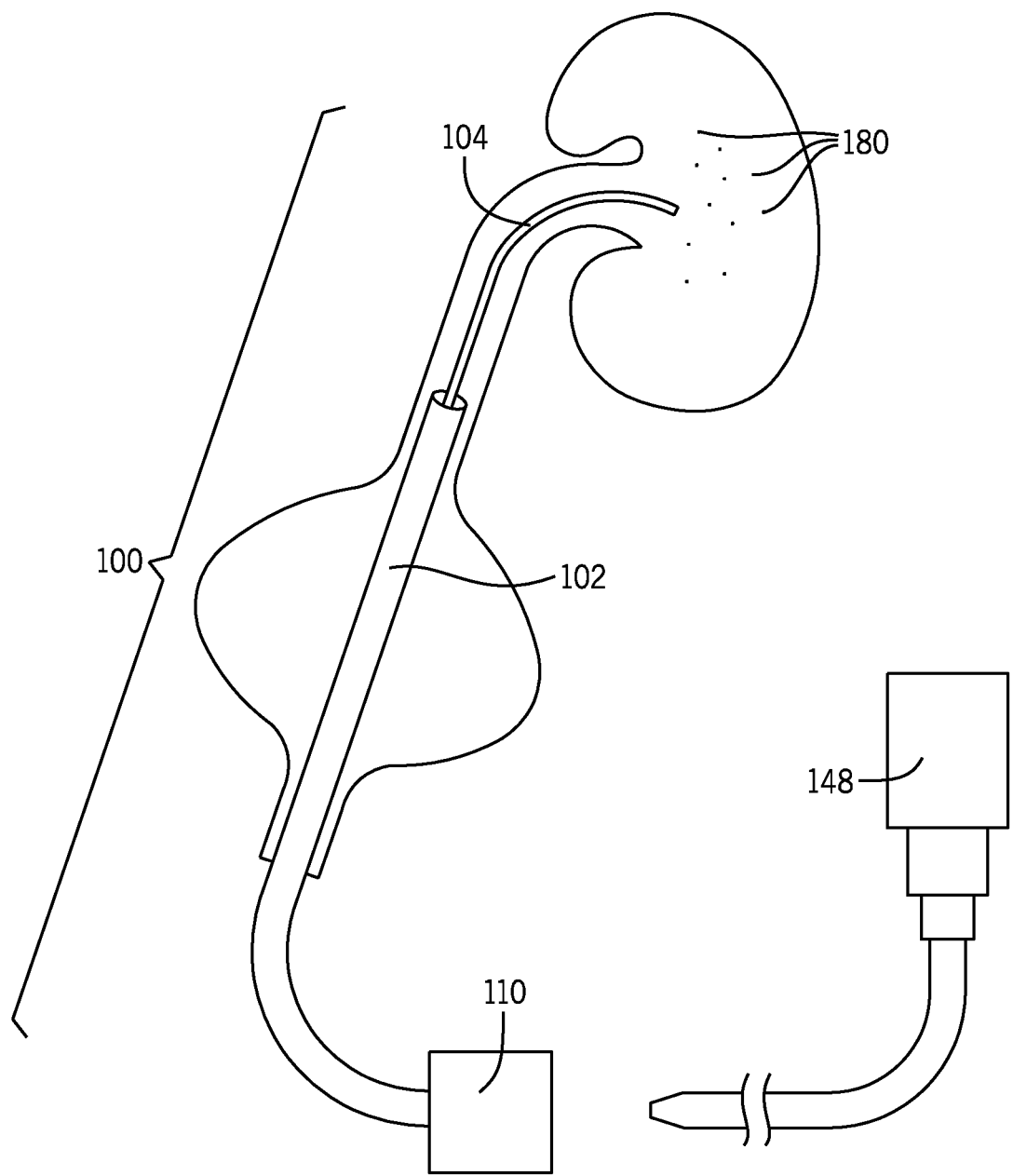
FIG. 6 is a partial schematic view of the removal device of FIG. 1 further including a valve that is in communication with a suction source.

Now turning to FIG. 5, portions of the removal device 100 may optionally be positioned in the passageway with the assistance of a positioning device, for example, such as an introducer core 108. The introducer core 108 includes a rigid, elongate body 170 with a rounded groove 172 extending longitudinally therethrough. The groove 172 preferably has a contour that accommodates the navigation mechanism 106 (e.g., guidewire). For example, in one configuration, the groove 172 is preferably rounded to accommodate a substantially cylindrical guidewire.

The body 170 of the introducer core 108 terminates at a tapered tip 174 at an end 176 thereof. The tip 174 includes a taper that allows the introducer core 108 to be more easily inserted into the patient (i.e., through the patient's urethra). The introducer core 108 is adapted to be disposed in at least one of the passageways of the removal device 100 to provide support thereto. In one configuration, the introducer core 108 is inserted into the sheath 102. In a different configuration, the introducer core 108 is inserted into a portion of the vacuum tube 104 (e.g., through the first or second passageway 142, 144, respectively).

The introducer core 108 may be utilized in one or more of the passageways in the removal device 100 to assist with positioning thereof. In a preferred configuration, the introducer core 108 is inserted into the first passageway 142 of the vacuum tube 104 to assist in placement thereof. The introducer core 108 preferably extends substantially the entire length of the first passageway to provide a rigid support for the vacuum tube 104 as the vacuum tube 104 is being positioned in the passageway (e.g., urinary tract). The introducer core 108 is preferably detachable such that it may be removed from the second passageway 142 (or other portion of the removal device 100) after placement of the vacuum tube 104 is complete.

The removal device 100 is designed to be optionally utilized with the valve 110 (See FIG. 6) that is in fluid communication with the suction source 148 and is capable of controlling the suction associated with the vacuum tube 104. In one configuration, the valve 110 is a gate valve and may be designed to accommodate tubes and/or portions of the removal device 100 having varying diameters. The valve 110 preferably includes at least two different states, whereby the suction is supplied to the removal device 100 in a first state (i.e., via the vacuum tube 104), and whereby the suction is not supplied to the removal device 100 in a second state. The valve 110 may also include intermediate states that allow the suction to be supplied at a specified level. The valve 110 may further include a safety feature such as an auto-shut down mechanism that terminates the suction once a threshold pressure is breached. Other types of valves may be utilized in conjunction with the removal device as known in the art.

The valve 110 is adapted to be in communication with the suction source 148 via a tube or other mechanism. In one configuration, the suction source 148 is a wall suction as known in the art. In a different configuration, the suction source 148 may be a standard suction unit that is stationary or otherwise portable. In a further configuration, the suction source 148 may be supplied in some other way. In one configuration, a suction source 148 capable of supplying a pressure of about −22 mmHg is utilized, although it should be appreciated that the suction source 148 may supply other pressures as desired.

The removal device 100 may optionally include a sealable port (not shown), for example, such as one that uses a stopcock valve, for infusing or otherwise providing a liquid or other substance into the device 100. In one configuration, saline is infused through one or more of the passageways of the removal device 100 described herein. In this configuration, the suction may be off or paused. In a different configuration, the suction may be used to assist in transporting or otherwise moving the substance through the removal device 100.

Now turning to the use of the removal device 100. In one configuration, the removal device 100 is adapted to be used in a medical setting. In particular, the removal device 100 may be used to remove debris or another foreign object (e.g., kidney stone, diseased tissue, and the like) from a patient (not shown). The debris may reside in one or more organs, orifices, or passageways. Accordingly, the removal device 100 may be utilized in any passageway to assist in removing debris therefrom or adjacent thereto.

In one configuration best seen in FIGS. 7 and 8, the removal device 100 is designed to be positioned in a patient's urinary tract. As depicted in FIG. 7, the sheath 102 is inserted into the patient's urethra (not shown) and extends through the bladder 122 and ureter 112 until being positioned proximate a kidney stone(s) 118, which is most likely disposed in a portion of the urinary tract (e.g., adjacent the kidney 116). The ureterscope 134 (or other viewing instrument) is inserted into the sheath 102 along with the navigation mechanism 106. The ureterscope 134 and navigation mechanism 106 are pushed through the sheath 102 until extending through substantially the entirety thereof. The ureterscope 134 is used to fracture the kidney stone(s) 118 into fragments 180 (see FIG. 8) via a laser or other similar device. After the kidney stone(s) 118 are fractured, the ureterscope 134 is removed from the sheath 102, and preferably, the navigation mechanism 106 is retained within the sheath 102. Alternatively, in a different configuration, the navigation mechanism 106 may be removed.

As shown in FIG. 8, the vacuum tube 104 is thereafter inserted into the sheath 102 and utilizes the navigation mechanism 106 for guidance thereof. The introducer 108 is disposed within the vacuum tube 104 (e.g., in the first passageway 142) to maintain open communication through the passageways in the vacuum tube 104 during insertion into the patient. Additionally, the second passageway 144 of the vacuum tube 104 is aligned with the navigation mechanism 106. As the vacuum tube 104 is pushed through the sheath 102 (via the introducer 108), the navigation mechanism 106 aligns the second passageway 144 and guides the vacuum tube 104 to the fragments 180. Once the vacuum tube 104 is positioned adjacent the fragments 180, the introducer 108 is detached and removed therefrom. Once the introducer 108 has been removed, the valve 110 is opened to allow access to the suction source 148 and the fragments 180 are pulled from the patient through the removal device 100. A catch or basket (not shown) may be utilized outside of the patient (or in a portion of the removal device 100) to collect the fragments 180, biopsied tissue, and/or other debris.

It should be noted that the removal device 100 may be utilized in the manner described herein without fracturing the kidney stone(s) 118. In particular, the kidney stone(s) may be removed directly so long as they are sized to pass through the removal device 100. The removal device 100 described herein is capable of removing debris having varying sizes. For example, the removal device 100 is designed to remove debris that are characterized as particles of dust (e.g., about 0.001 μm to about 10,000 μm).

The removal device 100 is also designed to remove small, medium, and large kidney stones or other debris. For example, in one configuration, the removal device 100 is designed to remove kidney stones having an approximate diameter of between about 0.0001 mm to about 8 mm. In a different configuration, the removal device 100 is designed to remove kidney stones having an approximate diameter of between about 0.1 mm to about 6 mm. In a different configuration, the removal device 100 is designed to remove kidney stones having an approximate diameter of between about 1 mm to about 5 mm. In still a different configuration, the removal device 100 is designed to remove kidney stones having an approximate diameter of between about 2 mm to about 4 mm. It should be noted that, in one configuration, the removal device 100 described herein is designed to be utilized as described and does not utilize the working channel of a device (i.e., a ureterscope).

In a further configuration, the removal device 100 is designed for other medical uses, such as, to treat bladder stones and for use with other less invasive procedures, such as percutaneous stone removal, laparoscopic procedures, spine procedures, arthroscopic surgery, and microsurgery (e.g., to treat knee, ankle, foot, and hand issues). The removal device 100 may also be used to remove dead tissue, masses, and other debris. In a further configuration, the removal device 100 is used in a biopsy procedure.

The removal device 100 may be utilized in conjunction with visualization mechanisms including with, for example, fluoroscopy, ultrasound, computerized tomography (CT) scans, and magnetic resonance imaging. One or more portions of the removal device 100 may further comprise one or more radio opaque markers (not shown) and/or radio opaque materials to assist in inserting, positioning, and/or removing the removal device 100. For example, a radio opaque marker may be disposed adjacent an end of the vacuum tube 104 and/or navigation mechanism 106 to assist in the positioning thereof. The marker may be visible to a physician under X-ray, fluoroscopy, or other visual aids. The removal device 100 may include one or more radio opaque markers on other portions thereof, including on the sheath 102, the introducer core 108, or other portions thereof. In use, the physician may use the mark(s), for example, to facilitate placement of the removal device 100 in the patient.

In one particular configuration, the removal device 100 is used in conjunction with fluoroscopy. In another configuration, the removal device 100 is used in conjunction with a cystoscope, miniature camera, or other visualization device. In this configuration, the removal device 100 is not inserted into or utilized by the working channel of the cystoscope. Rather, the cystoscope should have a relatively small diameter (e.g., less than about 3 mm) and the removal device 100 is used in conjunction (separately) therewith or designed as a system with direct visualization and the removal device. A navigation mechanism 106 may optionally be used in this configuration to guide the cystoscope and/or the removal device 100 to the desired location.

One or more portions of the removal device 100 including the sheath 102, the vacuum tube 104, the introducer core 108, and/or the navigation mechanism 106 may include a hydrophilic or hydrophobic coating and/or may comprise a hydrophilic or hydrophobic material. In some configurations, the vacuum tube 104 is coated with a lubricious hydrophilic coating. In one configuration, the coating may be applied to any portion of the sheath 102 to reduce irritation caused by contact with the surrounding tissue in the urinary tract and/or bladder. In another configuration, the coating is applied to portions of the first passageway 142 of the vacuum tube 104 to facilitate debris removal therethrough. In another configuration, the coating is applied to portions of the second passageway 144 of the vacuum tube 104 to facilitate the guidance of the navigation mechanism 106 therethrough. The coating is preferably compatible with the materials used. In one particular configuration, the preferred coating is heparin, although it should be appreciated that other coatings may be utilized. Additionally, one or more portions of the removal device 100 may incorporate a material having the properties as described herein.

In a different configuration, the removal device 100 is used in non-medical applications. In particular, in one configuration, the removal device 100 is used to remove debris from a confined space, such as a hydraulic line, a plumbing line, and/or a petrochemical line, before, during, and/or after repairs to the line(s). The removal device 100 itself may be used to assist in repairing the line(s). Other non-medical uses include the use of the removal device 100 in ventilation systems such as heating and cooling systems and within mechanical or industrial pipes.

Thus, systems and methods are disclosed that are particularly advantageous for addressing the ureter and kidney using an aspirator. For example, some traditional devices treat attempt to meet clinical needs with a separate or dedicated aspirator. However, in the present disclosure, the aspirator may be inserted over a guidewire after a treatment, such as a ureteroscopy with laser, has been performed.

The present invention has been described in terms of one or more preferred embodiments, and it should be appreciated that many equivalents, alternatives, variations, and modifications, aside from those expressly stated, are possible and within the scope of the invention.

I claim:

1. A method for removing an object, comprising:
guiding a flexible tube having an external diameter of at least about 11 French through a passageway of an in vivo subject using an introducer configured to provide support to the flexible tubing during insertion of the flexible tube, wherein the flexible tube comprises at least a first passageway and a second passageway encompassed by the first passageway and the introducer is configured to pass through the first passageway and accommodate the second passageway in a groove during insertion of the flexible tube through the passageway of the in vivo subject;
positioning a distal end of the first passageway adjacent to the object;
infusing liquid through the second passageway, wherein the liquid comprises saline solution; and
causing suction to be applied by a suction source coupled, via a valve, to a proximal end of the first passageway to remove the object and at least a portion of the liquid through the first passageway after infusion of the liquid through the second passageway.

2. The method of claim 1, wherein suction is caused to be applied simultaneously with infusion of at least a second portion of the liquid through the second passageway.

3. The method of claim 1, further comprising:
inserting a sheath in the passageway of the in vivo subject;
inserting a device into the passageway of the in vivo subject through the sheath;
positioning the device adjacent to a second object;
using the device to break the second object into a plurality of objects including the object;
removing the device from the sheath; and
wherein the flexible tube is guided through the sheath subsequent to removal of the device from the sheath.

4. The method of claim 3, wherein the second object has a diameter greater than about 10 millimeters and cannot be removed through the first passageway, and the object has a diameter less than about 4.33 millimeters.

5. The method of claim 1, wherein the flexible tube has an external diameter that is less than or equal to about 13 French.

6. The method of claim 1, further comprising causing suction to be paused during a procedure to remove the object.

7. The method of claim 6, wherein causing suction to be paused comprises causing suction to be paused during infusion of the liquid through the second passageway.

8. A method for removing an object, comprising:
guiding a tube having an external diameter of at least about 11 French into a natural passageway of an in vivo subject using an introducer configured to provide support to the tube during the insertion of the tube, wherein the tube comprises at least a first passageway and a second passageway encompassed by the first passageway and the introducer is configured to pass through the first passageway and accommodate the second passageway in a groove during insertion of the tube through the natural passageway of the in vivo subject;
positioning a distal end of the first passageway adjacent to the object;
infusing liquid through the second passageway, wherein the liquid comprises saline solution; and
causing suction to be applied by a suction source coupled, via a valve, to a proximal end of the first passageway to remove the object and at least a portion of the liquid through the first passageway after infusion of the liquid through the second passageway.

9. The method of claim 8, wherein suction is caused to be applied simultaneously with infusion of at least a second portion of the liquid through the second passageway.

10. The method of claim 8, further comprising:
inserting a sheath in the natural passageway of the in vivo subject;
inserting a device into the passageway of the in vivo subject through the sheath;
positioning the device adjacent to a second object;
using the device to break the second object into a plurality of objects including the object;
removing the device from the sheath; and
wherein the tube is guided through the sheath subsequent to removal of the device from the sheath.

11. A method for removing an object, comprising:
guiding a tube through a passageway of an in vivo subject using an introducer configured to provide support to the tube during insertion of the tube, wherein the tube has an external diameter that is at least about 11 French and less than or equal to about 13 French and comprises at least a first passageway and a second passageway encompassed by the first passageway and the introducer is configured to pass through the first passageway and accommodate the second passageway in a groove during insertion of the tube through the passageway of the in vivo subject;
positioning a distal end of the first passageway adjacent to the object;
infusing liquid through the second passageway; and
causing suction to be applied by a suction source coupled, via a valve, to a proximal end of the first passageway to remove the object through the first passageway.

12. The method of claim 11, wherein suction is caused to be applied simultaneously with infusion of the liquid through the second passageway.

13. The method of claim 11, wherein further comprising causing suction to be paused during a procedure to remove the object.

14. The method of claim 11, further comprising:
inserting a sheath in the passageway of the in vivo subject;
inserting a device into the passageway of the in vivo subject through the sheath;
positioning the device adjacent to a second object;
using the device to break the second object into a plurality of objects including the object;
removing the device from the sheath; and
wherein the tube is guided through the sheath subsequent to removal of the device from the sheath.

15. A method for removing a plurality of objects, comprising:
guiding a tube having an external diameter of about 11 French through an in vivo subject's urethra using an introducer configured to provide support to the tube during insertion of the tube;
positioning a distal end of a first passageway adjacent to the plurality of objects;
infusing liquid through a second passageway, wherein the liquid comprises saline solution and the second passageway is encompassed by the first passageway and the introducer is configured to pass through the first passageway and accommodate the second passageway in a groove during insertion of the tube through the in vivo subject's urethra; and causing suction to be applied by a suction source coupled, via a valve, to a proximal end of the first passageway to substantially concurrently remove the plurality of objects and at least a portion of the liquid through the first passageway after infusion of the liquid through the second passageway, wherein each of the plurality of objects has a diameter less than about 4.33 millimeters.

16. The method of claim 15, wherein suction is caused to be applied simultaneously with infusion of the liquid through the second passageway.

17. The method of claim 15, further comprising:
inserting a sheath in the in vivo subject's urethra;
inserting a device into the in vivo subject's urethra through the sheath;
positioning the device adjacent to an object;
using the device to break the object into the plurality of objects;
removing the device from the sheath; and
wherein the tube is guided through the sheath subsequent to removal of the device from the sheath.

\* \* \* \* \*